(12) United States Patent
Boehm, Jr. et al.

(10) Patent No.: US 6,972,005 B2
(45) Date of Patent: Dec. 6, 2005

(54) DUAL CHAMBER SYRINGE AND DUAL LUMEN NEEDLE

(76) Inventors: Frank H. Boehm, Jr., 2408 Genesee St., Utica, NY (US) 13501; Benedetta D. Melnick, 1406 Schuyler St., Rome, NY (US) 13440

(*) Notice: Subject to any disclaimer, the term of this patent is extended or adjusted under 35 U.S.C. 154(b) by 120 days.

(21) Appl. No.: 10/289,682

(22) Filed: Nov. 7, 2002

(65) Prior Publication Data

US 2004/0092864 A1 May 13, 2004

Related U.S. Application Data

(60) Provisional application No. 60/379,371, filed on May 10, 2002.

(51) Int. Cl.[7] .......................... A61M 5/00; A61M 5/31; B67D 5/52; B67D 5/60
(52) U.S. Cl. ...................... 604/191; 604/240; 222/135; 222/145.5
(58) Field of Search .................. 604/27, 36, 38, 604/46, 48, 82, 93.01, 181, 187, 191, 218, 604/240, 241, 242, 243, 264, 275, 284, 533, 604/534, 535; 222/135, 137, 145.1, 145.4, 222/145.5

(56) References Cited

U.S. PATENT DOCUMENTS

| | | | | |
|---|---|---|---|---|
| 2,112,160 A | * | 3/1938 | Johnson | 604/518 |
| 4,260,077 A | * | 4/1981 | Schroeder | 222/137 |
| 4,979,942 A | * | 12/1990 | Wolf et al. | 604/83 |
| 5,033,650 A | * | 7/1991 | Colin et al. | 222/137 |
| 5,116,315 A | * | 5/1992 | Capozzi et al. | 604/82 |
| 5,665,067 A | * | 9/1997 | Linder et al. | 604/82 |

* cited by examiner

*Primary Examiner*—Nicholas D. Lucchesi
*Assistant Examiner*—Mark K. Han
(74) *Attorney, Agent, or Firm*—Dilworth & Barrese LLP

(57) ABSTRACT

A syringe assembly for administering a variety of fluids includes a syringe provided with a plurality of flow-isolated chambers, each of which is in flow communication with a respective lumen of a multi-lumen needle located downstream from the syringe. Each lumen is flow-isolated from the rest of the lumens and guides a respective one of the variety of fluids toward an outlet port formed in the needle so that the fluids mix with one another only upon exiting the outlet port.

19 Claims, 1 Drawing Sheet

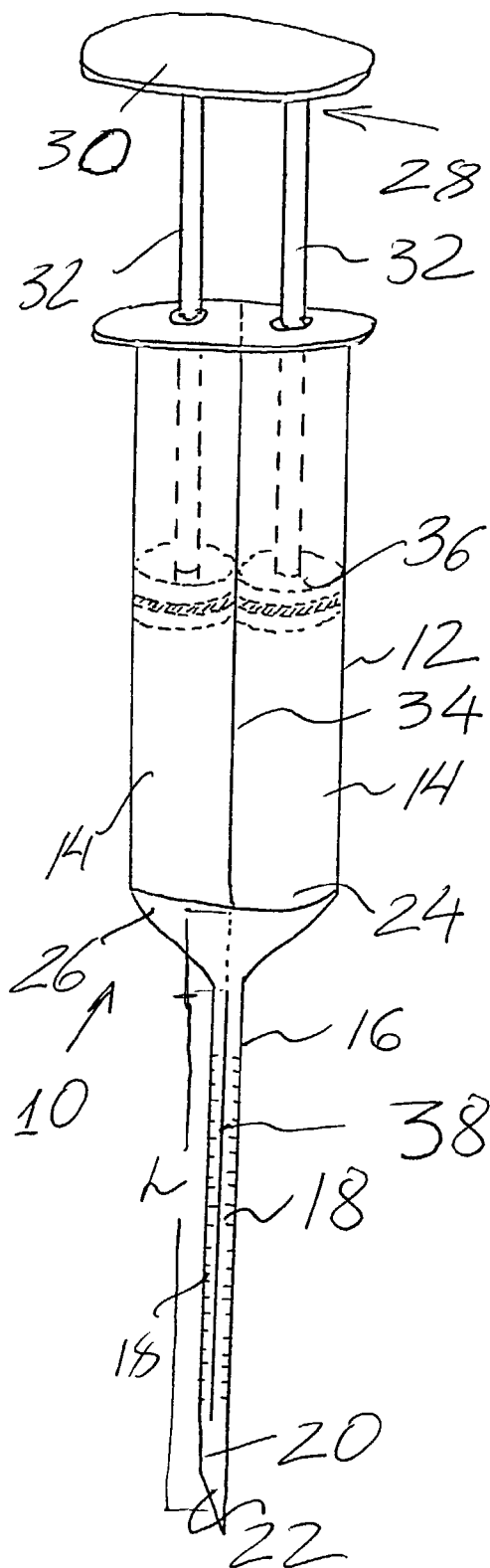
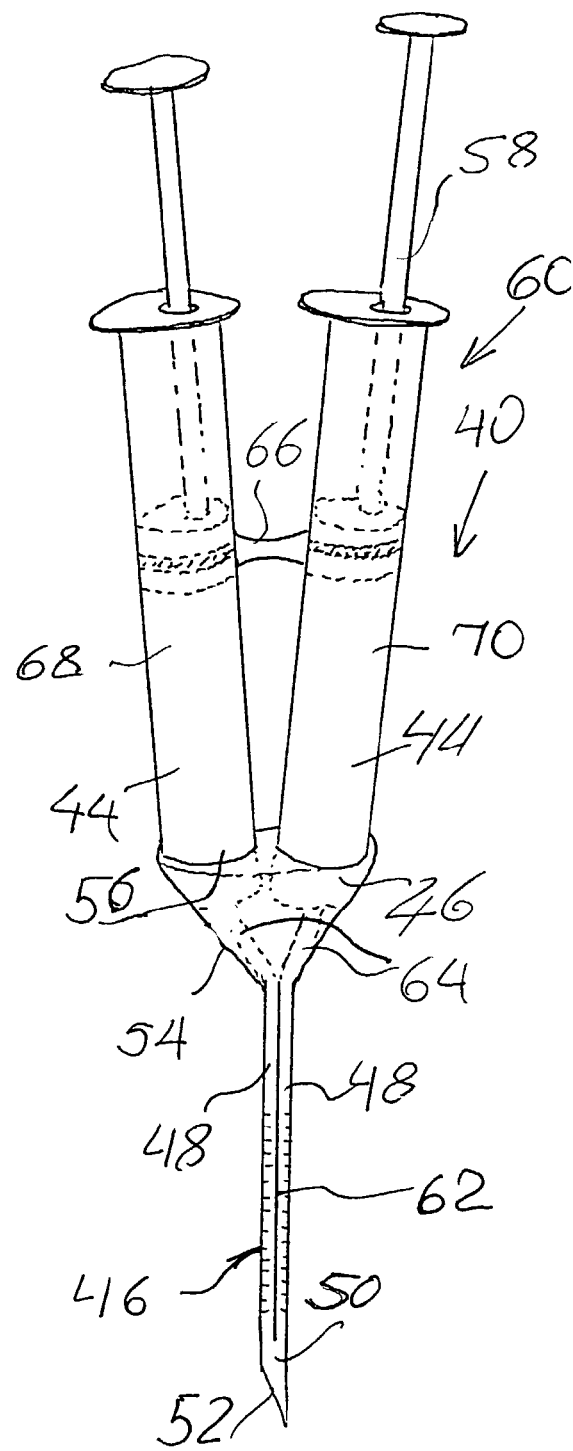
FIG. 1
FIG. 2

DUAL CHAMBER SYRINGE AND DUAL LUMEN NEEDLE

CROSS REFERENCE TO RELATED APPLICATION

This application is based on and claims Priority of Provisional Application Ser. No. 60/379,371 filed May 10, 2002 under 35 U.S.C. sctn. 119 (e).

BACKGROUND OF THE INVENTION

1. Field of the Invention

The present invention relates to syringes, and in particular to a syringe having a dual chamber and dual lumen needle for delivery of two separate fluids simultaneously, or consecutively, without mixing of the fluids until the fluid is delivered to its intended location.

2. Description of the Related Art

Syringes having multiple chambers for delivering multiple fluids, medications, solutions, and the like are well known. These syringes can deliver the fluids simultaneously or consecutively depending on the intentions of the health care professional administering the fluids. In the known dual chamber syringes, the fluids are expelled by depressing the plunger of the syringe to cause the fluid to be injected through the needle to which the chambers are attached. The needle is typically a single lumen needle, and if the fluids in the multiple chambers are injected simultaneously, the fluids are mixed in the single lumen needle as they are delivered into the patient's body. If the fluids are delivered consecutively, the fluids pass through the same lumen and into the patient's body.

The known single lumen needle is acceptable for use with fluids that are compatible with each other and which do not adversely react with each other. For fluids that adversely react with each other, two separate syringes must be used, having their own needles, and the doctor or nurse administering the fluid must be highly skilled to deliver the fluids simultaneously to the intended site so that mixing may occur only at the site. An example of fluids that react adversely for delivery through a single lumen needle are the components of fibrin glue material, which may be used to seal leaks in fluid filled vessels in the body, in particular the dura mata of the spinal cord. These components, such as platelets and fibrin, react with each to form a glue-like material. Delivering these through a single lumen needle, either simultaneously or consecutively, would clog the needle and render it useless.

Therefore a need exists for a syringe capable of delivering fluids from multiple chambers simultaneously or consecutively, which prevents reaction between the fluids during delivery.

SUMMARY OF THE INVENTION

There is provided a multiple chamber syringe having a needle with multiple lumens to ensure delivery of the fluids to a desired location in a patient without mixing of the fluids until the fluids are substantially at the desired location. Preferably, the syringe has two chambers, each having a plunger, which may be joined together by a harness to allow for simultaneous delivery of the fluids in the chambers. The plungers can also be depressed consecutively to allow for delivery of one fluid followed by the other. There is also provided a needle having two lumens, with each lumen in communication with a chamber of the syringe. The dual lumens preferably extend for the substantial length of the needle, and are joined adjacent to the tip of the needle so that the fluids are mixed upon exiting the needle.

The syringe of the present invention is particularly suited for the delivery of fluids that react with other upon contact, such as the components of fibrin glue. These components, typically fibrin and platelets, react with each other upon contact to form the glue-like material which may be used to seal leaks in fluid-filled vessels and cavities, such as the dura mater of the spinal cord. The dual lumen needle of the syringe prevents clogging, permitting the accurate delivery of the fibrin glue material to the leak in the vessel. Preferably, the needle has graduations on its surface for calibrating the depth to which the needle is inserted into the patient's body.

BRIEF DESCRIPTION OF THE DRAWINGS

The above and other objects, features and advantages will become more readily apparent from the following detailed description of the preferred embodiment accompanied by the flowing drawings, in which:

FIG. 1 is an elevational view of a syringe assembly in accordance with one embodiment of the invention; and FIG. 2 is an elevational view of the syringe assembly in accordance with another embodiment of the invention.

DETAILED DESCRIPTION OF THE PREFERRED EMBODIMENT

A syringe assembly 10, as illustrated in FIGS. 1 and 2, is operative to deliver a variety of fluids to a desired location either simultaneously or sequentially in response to the creation of a positive pressure at the upstream end of the syringe assembly. Particularly, the syringe assembly 10 includes a syringe 12 provided with a plurality of flow isolated chambers 14 which may store fluids that, if reacted with one another, can produce a mixture characterized by high density and low viscosity. Such a mixture conveyed through a fluid conveying conduit, particularly via such a small-dimensioned fluid conduit as a needle 16, tends to clog the passage rendering the needle 16 unusable. To minimize the risk of having the needle 16 inoperative, a plurality of flow isolated lumens 18 extending along a major part of the entire length L of the needle 16 open into a downstream region 20 of the needle in which the variety of fluids mix upon exiting an outlet port 22. Accordingly, each of the variety of fluids runs along a path isolated from other paths until it reaches the very bottom or downstream region 20 of the needle 16, where the risk of clogging the needle 16 is minimal because the mixed fluids have a relatively high velocity and pass through a relatively small needle volume formed adjacent to the outlet port 22.

Structurally, the syringe 12 and the needle 16 of the syringe assembly 10 are preferably two separate components detachably coupled to one another in a leak-free manner. Since the inner diameter of the needle 16 is substantially smaller than that of the syringe 12, the needle's upstream end 26 has a cross section widening towards a downstream end 24 of the syringe 12 and, preferably, provided with a conical shape, which is instrumental in accelerating fluid flow as fluid runs from the syringe 12 into the needle 16. Numerous techniques can be utilized for coupling the components together. For example, either the downstream end 24 of the syringe 12 can be provided with an outer or inner thread mating a respective thread on an opposing surface of the upstream end 26 of the needle 16. Alternatively, the needle 16 and the syringe 12 can be attached in a snap-in manner wherein the mating ends of these components are dimensioned to tightly fit one another in response to an external force applied to the components. Regardless of the way the components are coupled, the needle 16 and the syringe 12 have to be detachably assembled in a fluid-proof manner to prevent a leak of fluids upstream from the outlet port 22.

Alternatively, the syringe assembly 10 can be formed as a monolithic body having an upstream part formed as the syringe 12 and downstream part functioning as the needle 16. However, while such a structure is leak proof, administering fluids is not as convenient as it would be with a multi-part structure because of the difficulty of reaching a desired location within a human or animal body associated with the flexibility of the syringe assembly 10. A multi-part syringe assembly can be more flexible than the monolithic body.

Frequently, the delivery of the fluids should be administered simultaneously. As shown in FIG. 1, the syringe assembly 10 provides the user with an actuating mechanism 28 including a harness 30 which couples and synchronously actuates plungers 32, each of which provide a positive pressure in an upstream region of a respective chamber 14. The harness 30 can be removably attached to proximal ends of the plungers 32, which, thus, can be actuated separately to deliver the fluids in a sequential manner upon dismounting the harness 30. The scope of the invention is not limited to a dual-chamber/dual lumen syringe assembly and encompasses as many chambers and lumens as practically feasible. In case of three or more chambers, the harness 30 may be configured to selectively engage a desired number of the plungers 32 to provide any particular combination of fluids delivered to a desired location. To provide selective couplings, the harness 30 can be configured to include multiple segments displaceable relative one another so that, for example, if it is necessary to deliver a mixture of two fluids from a three-chamber syringe 12, the harness 30 would rigidly bridge only two plungers 32 leaving, thus, the third plunger idle during displacement of the bridged plungers.

A fluid impermeable partition 34 compartmentalizing the syringe 12 defines the flow isolated chambers 14 each of which is dimensioned and shaped to correspond to a respective piston 36 of the plungers 32. The partition 34 can extend beyond the downstream end 24 of the syringe 12 and be dimensioned so that when the needle 16 is mounted on a downstream stretch 38 of the partition 34, the latter forms two lumens 18. Alternatively, the needle 16 can be provided with a respective partition forming the lumens 18 and having a means for attaching the partitions of the syringe 12 and the needle together. Attachment of two partitions can be realized by a variety of systems which, among others, may include a keyed surface formed on one of the opposing ends of the partitions and a complementary shaped projection formed on the other end and received in a slot or simply having opposing surfaces of the partitions extend complementary to and in contact with one another.

Referring to FIG. 2, an alternative embodiment of the invention relates to a syringe assembly 60 which, similarly to the previously disclosed embodiment, includes a syringe 40 and a needle 46 provided with multiple fluid isolated chambers 44 and lumens 48, respectively. Generally, the syringe assembly 60 is designed to sequentially deliver fluids from the fluid isolated chambers 44.

In particular, the syringe 40 includes separate syringe units 68, 70, each provided with a respective chamber 44, and with a plunger 58 actuated to generate a positive pressure along an upstream stretch of the chamber 44 causing fluid to run via a respective lumen 48 to an outlet port 52. To attach the needle 50 and either one unit of or both syringe units 68, 70 of the syringe 60 together, the upstream end 46 of the needle 50 is formed with a conical flange 54 having nests 56 each if which is configured to receive a downstream end of the syringe units 68, 70. The nests 56 are configured to sealingly engage the downstream ends of the syringe units, but shaped so as to allow slight displacement of the received unit or units to establish a desired position convenient for a user. In use, the syringe units are spaced from another upon attachment with the needle 50 to allow the user to position one of his/her fingers between the syringe units. To reinforce the entire syringe assembly 60 and to prevent accidental displacement of the syringe units 68, 70, a strap 66 couples the syringe units together. The strap 66 can be made from shape memory material facilitating an administering procedure for the user who establishes the desired position of the syringe units once and for all.

Fluid communication between each of the syringe units 68, 70 of the syringe 60 and a respective lumen 48 is provided by fluid conveying channels 64 which can be formed either on the downstream end of the syringe units 68, 70 or on the upstream end of the lumens 48.

Thus, the inventive syringe assembly can be used for selectively or simultaneously delivering a variety of fluids to a desired location and has a simple and effective structure facilitating attachment of separate components of the syringe assembly while minimizing the risk of clogging these components during the repeated use of the inventive assembly. While several embodiments of the disclosure have been described herein, the above description should not be construed as limiting, but merely an exemplification of preferred embodiments as interpreted within the scope of the claims appended hereto.

What is claimed is:

1. A syringe assembly for delivering a variety of fluids to a desired location, comprising:

a syringe configured to have a plurality of flow isolated chambers each receiving a respective one of the variety of the fluids; and a needle formed with spaced upstream and downstream ends defining therebetween a length of the needle, the needle having a plurality of flow isolated lumens each in flow communication with a respective chamber and extending a length of the needle from the upstream end toward and joining one another adjacent to the downstream end of the needle wherein the syringe has a body defining the plurality of flow isolated chambers in flow communication with the needle; and, the downstream portion of the body is provided with a frustoconical cross section narrowing toward the needle, a fluid impermeable partition extending through the needle and terminating adjacent to the downstream end of the needle to define the plurality of lumens.

2. The syringe assembly of claim 1, further comprising a plurality of plungers each received in a respective one of the plurality chambers and operative to create a positive pressure sufficient to drive fluid from the respective chamber along the lumen into the downstream end of the needle, wherein the downstream end of the needle is provided with an outlet port.

3. The syringe assembly of claim 2, wherein the plurality of plungers are selectively actuable to guide the variety of fluids in a sequential manner towards the outlet port of the needle.

4. The syringe assembly of claim 2, wherein the plurality of plungers are simultaneously actuable to guide the variety of fluids out from the plurality of chambers of the syringe through the plurality of lumens of the needle into the downstream end of the needle wherein the variety of fluids mix with one another upon exiting the outlet port located in the vicinity of the desired location.

5. The syringe assembly of claim 4, further comprising a harness operative to selectively couple the plurality of plungers simultaneously displaceable within respective flow isolated chambers of the syringe.

6. The syringe assembly of claim 4, wherein the plurality of chambers includes at least two chambers.

7. The syringe assembly of claim 1, wherein the body and the needle form a monolithic housing.

8. The syringe assembly of claim 1, wherein the body and the needle are removably attached to one another in a leak-free manner, the needle being provided with a fluid impermeable partition sealingly coupled to the fluid impermeable partition of the syringe.

9. The syringe assembly of claim 1, wherein the syringe has separate syringe units each defining a respective one of the plurality of flow isolated chambers, the upstream end of the needle being provided with a flange having fluid guiding channels sealingly attached to the flow isolated chambers and the lumens to convey fluid therebetween.

10. The syringe assembly of claim 9, wherein the separate syringe units each are detachably coupled to the flange provided with a plurality of sockets.

11. The syringe of claim 10, wherein the separate syringe units each are displaceably mounted to a respective socket of the flange, whereas a user is able to displace the separate syringe units relative to one another.

12. A method of delivering a variety of fluids to a desired location comprising the steps of:
  providing a syringe having a plurality of flow isolated chambers;
  supplying the variety of fluids so that each of the plurality of flow isolated chambers receives a respective one of the variety of fluids;
  providing a needle having a plurality of lumens in flow isolation with one another, each of the lumens being in flow communication with a respective chamber and having a cross-section substantially smaller than a cross-section of the respective chamber, the lumens extending a length of the needle and joining one another adjacent to an outlet port formed in a downstream end of the needle wherein
  the syringe has a body defining the plurality of flow isolated chambers in flow communication with the needle; and,
  the downstream portion of the body is provided with a frustoconical cross section narrowing toward the needle, a fluid impermeable partition extending through the needle and terminating adjacent to the downstream end of the needle to define the plurality of lumens; and
  guiding the variety of fluids through the flow isolated chambers via respective lumens into the downstream end of the needle.

13. The method of claim 12, wherein the variety of fluids are guided simultaneously, whereas the fluids are mixed in the downstream end of the needle upon exiting the outlet port.

14. The method of claim 12, wherein the variety of fluids are guided selectively in a sequential manner.

15. The method of claim 12, further comprising the step of displacing the flow isolated chambers relative to one another.

16. The method of claim 12, wherein the variety of fluids react with one another upon contact at the downstream end of the needle.

17. The method of claim 16, wherein the variety of fluids reacting with one another includes fibrin and platelets to form the glue-like material.

18. The method of claim 16, wherein the syringe and the needle form a monolithic body or a multi-part body, in which the syringe and the needle are detachably coupled to one another.

19. A syringe assembly for delivering a variety of fluids to a desired location, comprising:
  a syringe configured to have a plurality of flow isolated chambers each receiving a respective one of the variety of the fluids; and
  a needle formed with spaced upstream and downstream ends defining therebetween a length of the needle, the needle having a plurality of flow isolated lumens each in flow communication with a respective chamber and extending a length of the needle from the upstream end toward and joining one another adjacent to the downstream end of the needle; wherein,
  the syringe has a body defining the plurality of flow isolated chambers in flow communication with the needle; and,
  a fluid impermeable partition extends through the needle and terminates adjacent to the downstream end of the needle to define the plurality of lumens.

* * * * *